US005549608A

United States Patent [19]
Errico et al.

[11] Patent Number: 5,549,608
[45] Date of Patent: Aug. 27, 1996

[54] ADVANCED POLYAXIAL LOCKING SCREW AND COUPLING ELEMENT DEVICE FOR USE WITH ROD FIXATION APPARATUS

[75] Inventors: Joseph P. Errico, Hempstead, N.Y.; Thomas J. Errico, Summit; James D. Ralph, Oakland, both of N.J.

[73] Assignee: Fastenetix, L.L.C., Summit, N.J.

[21] Appl. No.: 502,285

[22] Filed: Jul. 13, 1995

[51] Int. Cl.⁶ ............................................. A61B 17/70
[52] U.S. Cl. ............................ 606/61; 606/73; 606/60
[58] Field of Search ........................... 606/61, 69, 70, 606/71, 72, 73, 66, 65, 59, 54, 104; 623/17, 16

[56] References Cited

U.S. PATENT DOCUMENTS

| | | |
|---|---|---|
| 4,805,602 | 2/1989 | Puno et al. |
| 4,946,458 | 8/1990 | Harms et al. ........................ 606/61 |
| 4,987,892 | 1/1991 | Krag et al. ......................... 606/61 |
| 5,151,103 | 9/1992 | Tepic et al. ........................ 606/69 |
| 5,176,680 | 1/1993 | Vignaud et al. .................... 606/61 |
| 5,190,543 | 3/1993 | Schläpfer .......................... 606/61 |
| 5,207,678 | 5/1993 | Harms et al. ....................... 606/61 |
| 5,217,497 | 6/1993 | Mehdian ........................... 623/17 |
| 5,261,909 | 11/1993 | Sutterlin et al. .................... 606/61 |
| 5,261,912 | 11/1993 | Frigg .............................. 606/61 |
| 5,306,275 | 4/1994 | Bryan ............................. 606/61 |
| 5,360,431 | 11/1994 | Puno et al. ........................ 606/72 |
| 5,443,467 | 8/1995 | Biedermann et al. ................ 606/65 |
| 5,480,401 | 1/1996 | Navas ............................. 606/61 |

*Primary Examiner*—Guy V. Tucker
*Attorney, Agent, or Firm*—Joseph P. Errico

[57] ABSTRACT

A polyaxial orthopedic device for use with rod implant apparatus includes a screw having a curvate head and a coupling element. The coupling element has a tapered lower portion including a slotted interior chamber in which the curvate head is initially polyaxially disposed; a recess formed in its side for receiving the rod of the implant apparatus; and an exterior threading disposed on its upper portion for receving thereon a top locking nut. A locking ring is disposed about the exterior of the lower portion of the coupling element, and provides an inward force on the outwardly tapered portion upon downward translation thereof, thereby causing the interior chamber to crush lock the screw head therein, thus eliminating the polyaxial nature of the screw-element coupling. In addition, a hollow cylindrical rod securing sleeve fits over the coupling element and locks the rod to the coupling element. In a first embodiment, the locking nut seats against the top of the sleeve, which seats against the top of the locking ring, and causes the sleeve to lock the rod and the screw in the interior chamber. In a second embodiment, the locking ring and the bottom of the coupling element have threads so that the locking ring may be translated separately to lock the screw.

18 Claims, 12 Drawing Sheets

ADVANCED POLYAXIAL LOCKING SCREW AND COUPLING ELEMENT DEVICE FOR USE WITH ROD FIXATION APPARATUS

BACKGROUND OF THE INVENTION

1. Field of the Invention

This invention relates generally to a polyaxial screw and coupling apparatus for use with orthopedic fixation systems. More particularly, the present invention relates to a screw for insertion into spinal bone, and a coupling element polyaxially mounted thereto for coupling the screw to an orthopedic implantation structure, such as a rod, therein enhancing the efficacy of the implant assembly by providing freedom of angulation among the rod, screw and coupling element.

2. Description of the Prior Art

The bones and connective tissue of an adult human spinal column consists of an upper portion having more than 20 discrete bones, and a lower portion which consists of the sacral bone and the coccygeal bodies. The bones of the upper portion are generally similar in shape, as will be more fully described hereinbelow with respect to FIGS. 1 and 2. Despite their similar shape, however, they do vary substantially in size in accordance with their individual position along the column and are, therefore, anatomically categorized as being members of one of three classifications: cervical, thoracic, or lumbar. The cervical portion, which comprises the top of the spine, up to the base of the skull, includes the first 7 vertebrae. The intermediate 12 bones are the thoracic vertebrae, and connect to the 5 lumbar vertebrae.

These bones of the upper portion vary in size, but are each similarly coupled to the next by a tri-joint complex. The tri-joint complex consists of an anterior disc and the two posterior facet joints, the anterior discs of adjacent bones being cushioned by cartilage spacers referred to as intervertebral discs. Referring now to FIGS. 1 and 2, top and side views of a typical vertebral body of the upper portion of the spinal column is shown. The spinal cord is housed in the central canal 10, protected from the posterior side by a shell of bone called the lamina 12. The lamina 12 has three large protrusions, two of these extend laterally from the shell and are referred to as the transverse process 14. The third extends back and down from the lamina and is called the spinous process 16. The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

The lower portion of the spinal column, which extends into the hip region is primarily comprised of the sacral bone. This bone is unlike the other bones of the spinal column, in both shape and size. In fact, at birth humans have five distinct sacral bones which begin to fuse together during childhood, and by adulthood have fully combined. FIGS. 3 and 4 show side and perspective views of a sacral bone connected to the lower lumbar vertebrae.

From the side, the sacral body 50 appears horn-shaped, having an anterior 52 and a posterior side 54. The perspective view, however, demonstrates the sacral bone to be more plate-shaped, having a thin, curvate profile. The posterior side 54 includes the sacral foramena 56 which are, in fact, the fused former lamina portions of the original articulated sacral bones. Beneath the sacral foramena 56, the sacral roots of the spinal cord (not shown) are housed. The anterior 52 portion of the sacral body is, therefore, understood to be the fused former vertebral bodies of the originally articulated sacral bones. Extending laterally from the sacral plate are two, opposing, sacro ala 58, which are related to the transverse processes of the upper vertebrae. The sacro ala mate with the hip bones at the sacro-iliac joint 60. The sacro-iliac joint provides stabilization and support for the base of the spinal column, affording little if any rotational movement in adults. The top of the posterior portion of the sacral bone, the sacral foramena 56, couple with the lowest lumbar vertebra 62.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. The present invention relates to spinal fixation devices for immobilizing and altering the alignment of the spine over a large number, for example more than three or four, vertebra by means of affixing at least one elongate rod to the sequence of selected bones.

Such "rod assemblies" generally comprise a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape.

It has been identified, however, that a considerable difficulty is associated with inserting screws along a misaligned curvature and simultaneously exactly positioning the coupling elements such that the receiving loci thereof are aligned so that the rod can be passed therethrough without distorting the screws. Attempts at achieving proper alignment with fixed screws is understood to require considerably longer operating time, which is known to increase the incidence of complications associated with surgery. Often such alignments, with such fixed axes devices could not be achieved, and the entire instrumentationing effort would end unsuccessfully.

In addition, for many patients specific pathology it is desirable that the rod extend down into and beyond the lumbar portion of the spine, and for the end of the rod to be coupled to the sacral bone. Providing such an end to the assembly in the sacral bone has been understandably suggested inasmuch as it provides superior support to the full extent of the assembly. The most suitable position for the insertion of the screws into the sacral body may not, however, conform to the direction extent of the rod as it is affixed to the entirety of the assembly. Misalignment of the rod with respect to the screw and the coupling element is often a source of considerable disadvantage for the surgeon, often requiring considerable efforts to be expended bending and aligning the rod with the receiving locus of the coupling element. These additional efforts are a considerable difficulty associated with the proper and expeditious affixation, and over the long term, the offset of the rod can have a deleterious effect on the overall performance of the entire implantation assembly.

The art contains attempts at providing instrumentation, for example as set forth in U.S. Pat. No. 5,207,678 to Harms et al., which permit a freedom with respect to angulation of the screw and the coupling element. These teachings, however, have generally been complex, and inadequately reliable with respect to durability. Foe example, U.S. Pat. No. 5,207,678, teaches a pedicle screw having a "spherical segment-shaped head". The screw is inserted through a first receiving element, into the pedicle, such that the spherical head is disposed in the curvate base of the first receiving element. Once properly angled, a second inner receiving element is positioned within the first receiving element. The rod, which is necessarily threaded is then positioned within the two nested receiving elements. Nuts on the rod, positioned on opposing sides of the receiving element are then simultaneously tightened relative to one another in order to lock the rod to the receiving elements. The locking of the nuts to the receiving element is further intended to lock the screw in the proper angulation with respect to the receiving elements and the rod.

The considerable drawbacks associated with such a system include the necessity to prepare the threaded rod with a pair of nuts, properly positioned along the extent of the rod, which must be individually tightened or moved during the implantation procedure. Manipulation of the nuts is tedious in the ideal preparation, and often requires removal and considerable adjustment of the nut positions even after a portion of the rod has been implanted.

An additional difficulty with the above described Harms et al. system is that it requires a plurality of elements, such as nesting receiving elements and multiple nuts, which negate the simplicity and efficiency of implantation which is desired in the surgical field.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial locking screw and coupling element for use with rod stabilization and immobilization systems in the spine. More particularly, the screw and coupling element assembly comprise a bone screw having a head which is curvate in shape, for example semi-spherical, and a coupling element mounted thereon so as to be rotationally free prior to the secure fixation of the rod thereto, and which is securely locked in a given angulation once the rod is received by the coupling element. The coupling element has a generally cylindrical main body portion, a locking ring, a removable external rod securing sleeve, and a top locking nut.

The coupling element may be conceptually divided into a lower socket portion, an intermediate rod receiving portion, and a top nut receiving portion. The lower socket portion includes an interior chamber having an opening at the bottom thereof. The interior chamber is ideally suited for receiving therein the head of the screw such that the screw and the coupling element are held together in a rotationally free relationship. The external surface of the socket portion includes at least one vertical slot which is provided so that the opening in the bottom of the element may expand to receive the head of the screw, which has a major diameter which is larger than the unexpanded opening, such that the head of the screw may enter into the interior chamber. The at least one slot resiliently expands to permit the head of the screw to enter, and subsequently contracts into its original position once the head is fully inserted, therein inhibiting the screw head from being retracted. The head of the screw and the interior chamber are, however, free to rotate relative to one another.

The exterior of the lower portion of the coupling element, into which the screw head is inserted, tapers outward slightly toward the bottom of the element, therein having a slightly wider diameter at the bottom than at the top thereof. A locking ring, having a diameter equal to, or greater than the top of the lower portion, but less than the diameter of the bottom of the lower portion, is initially disposed about the top of the lower portion. Displacement of the locking ring downward causes the at least one vertical slot in the lower portion of the coupling element to close, therein causing the inner surface of the interior chamber to move radially inward, contacting the head of the screw, and locking thereto.

The intermediate portion of the coupling element comprises a side receiving locus wherein the rod is mounted. More particularly, at a position above the lower portion, a section of the generally cylindrical body is removed therein providing a receiving locus into which a support rod may nest. In order that the rod may be securely held within the receiving locus, an external rod securing sleeve is provided. The external rod securing sleeve is generally cylindrical in shape, having a hollow center for sliding over the top of the coupling element. The opposing sides of the rod securing sleeve include vertically aligned opposing rounded slots, therein dividing the bottom of the sleeve such that it comprises two downwardly extending members. In other words, the slots provide the sleeve with a conformation which resembles an upside down u-shape.

The upper portion of the coupling element comprises a threading onto which a locking nut may be inserted, therein locking the rod securing sleeve onto the coupling element. The bottom surface of the nut is designed to mate with the top of the rod securing element. It is the engagement of the nut with the upper portion of the coupling element, and driving of the nut downward which causes the rod securing sleeve to be driven downward into its full rod locking position.

In a first embodiment, the inner wall of the locking ring and the outer surface of the lower portion of the coupling element are smooth. In addition, the bottom edge of the rod securing sleeve is designed to mate with the top surface of the locking ring of the lower portion of the coupling element. Subsequent to proper positioning of the screw into the bone, the nesting of the rod in the receiving locus, the setting of the proper angulation of the screw to the coupling element, and the positioning of the rod securing sleeve over the coupling element, the nut is placed on top of the coupling element and driven downward. The nut forces the sleeve downward, which in turn forces the locking ring downward to lock the screw within the interior chamber while simultaneously locking the rod and the rod securing sleeve.

In a second embodiment, the inner wall of the locking ring and the outer surface of the lower portion of the coupling element comprise mateable threadings, oriented such that proper rotation of the ring relative to the coupling element causes the ring to translate down the lower portion toward the bottom of the element. In the second embodiment, therefore, the locking ring may be independently driven downward along the lower portion of the coupling element to lock the screw to the coupling element. In this embodiment, the downward movement of the rod securing sleeve does not force the locking ring into its securing position. However, the interface of the bottom of the rod securing sleeve, once in place, does prevent the locking ring from counter-rotating and thereby loosening the screw and coupling element after implantation.

In both embodiments, each of the portions of the coupling element (lower, intermediate, and upper) include a central bore, aligned with one another, and which extends axially from the top of the coupling element into the interior chamber. The screw head correspondingly includes a recess, which is alignable with the central bore of the coupling element, whereby a screw-driving instrument may be inserted through the central bore, into the recess in the screw, and be utilized to drive the screw into the bone.

The first step in the process of implanting this embodiment of the invention is to insert the head of the screw into the interior chamber of the coupling element. Once it has been inserted, the angle of insertion at which the screw will have the greatest holding strength relative to the loading which the rod system will be applying thereto must be determined. Once this angle has been found, the screw and the coupling element are aligned with respect to one another so that a screw-driving tool may be inserted down the central bore of the coupling element, into the recess in the head of the screw, and thereby be rotationally inserted into the bone. Subsequent to the insertion of the screw, the screw-driving device is removed from the assembly, therein permitting the coupling element to rotate and change angular alignment relative to the screw.

In the second embodiment, in which the locking ring and the lower portion of the coupling element are threaded, the coupling element is positioned in anticipation of receiving the rod, and then the locking ring is rotated into a locking position thereby securing the relative angle of the screw and the coupling element. In the first embodiment, the locking of the screw to the coupling element by the translation of the locking ring is not possible without the rod securing sleeve being positioned.

The rod of each of the implantation apparatus is then provided into the side receiving locus in the intermediate portion of the coupling element. In the first embodiment the coupling element remains polyaxial so that it may be moved relative to the rod in order to optimize the placement thereof. In both embodiments, however, once the rod has been properly positioned, the securing sleeve is placed onto the coupling element, with the rod extending through the opposing vertical slots thereof. The top locking nut is then introduced onto the top of the coupling element.

In the second embodiment, the rod securing sleeve may be placed onto the coupling element to the full and proper extent once the rod has been positioned, provided the locking ring has been fully rotated downward. In contrast, in the first embodiment, as the securing sleeve descends onto the coupling element it is prevented from fully seating and securing the rod in place by the locking ring. The step of driving the top locking nut into position, however, provides the impetus required to drive the locking ring downward. In a preferred variation of this embodiment, the top of the ring interlocks with the bottom of the sleeve, thereby preventing a misfeed of the rod securing sleeve and the ring. In the first embodiment, therefore, the final act of driving the top locking nut down onto the upper portion of the coupling element: causes the rod securing sleeve to fully descend, therein locking the rod within the rod receiving locus; causes the locking ring to descend into its locking position along the lower portion, thereby locking the angulation of the screw to the coupling element; and prevents the securing sleeve from rising up off the coupling element.

It is understood that during assembly, the locking ring of the second embodiment may remain untightened until the rod and rod securing sleeve have been coupled to the polyaxial coupling element, so as to parallel the polyaxial assembly of the first embodiment, however, it may be preferable to tighten the locking ring prior to the placement of the rod has been placed. The use of a particular embodiment shall, therefore, be within the province of the surgeon, in accordance with the determination of the proper protocol for use with respect to each patient. It may be desirable for the entire rod system to employ some screw and coupling elements of the first embodiment, and others of the second embodiment, depending upon the sequence of their insertion.

In addition, it shall be understood that the curvate shape of the head of the screw may be chosen from the various specific shapes which are compatible with the general polyaxial concept of the present invention. For the purposes of providing specific variations of the embodiments described above, and set forth more fully hereinbelow with respect to the drawings, two possible shapes of the screw head are provided, the first being fully semi-spherical and the second being hemispherical (having a flattened top profile. The choice of using flattened top profile versus a fully semi-spherical profile is associated with the height of the overall screw and coupling element, the semi-spherical (or ball) head of the screw providing for a higher seating of the coupling element versus the hemispherical flattened head.

Multiple screw and coupling element assemblies are generally necessary to complete the full array of anchoring sites for the rod immobilization system, however, the screw and coupling element assembly of the present invention is designed to be compatible with alternative rod systems so that, where necessary, the present invention may be employed to rectify the failures of other systems the implantation of which may have already begun.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 2:
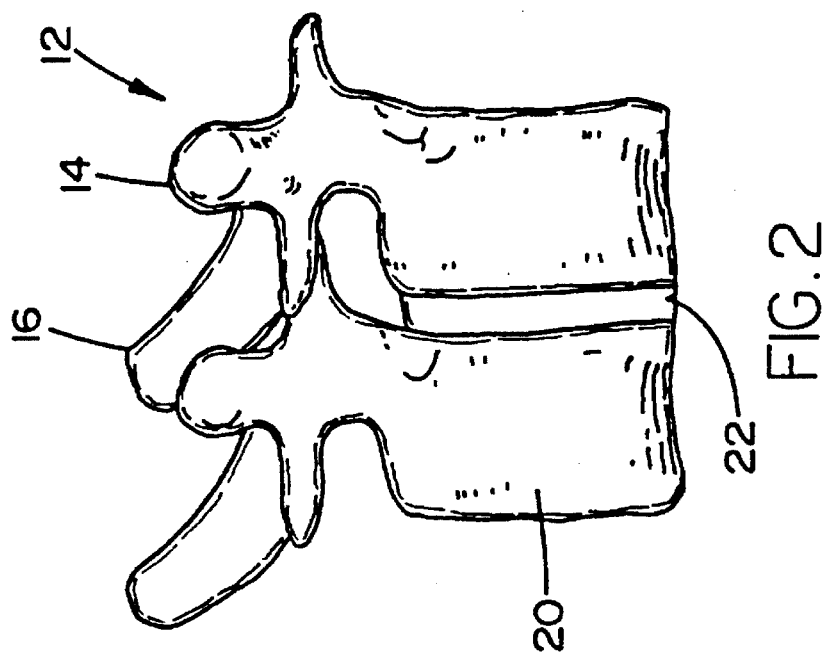
FIG. 2 is a side view of sequentially aligned vertebral bones, such as are found in the cervical, thoracic, or lumbar spine.
Figure 1:
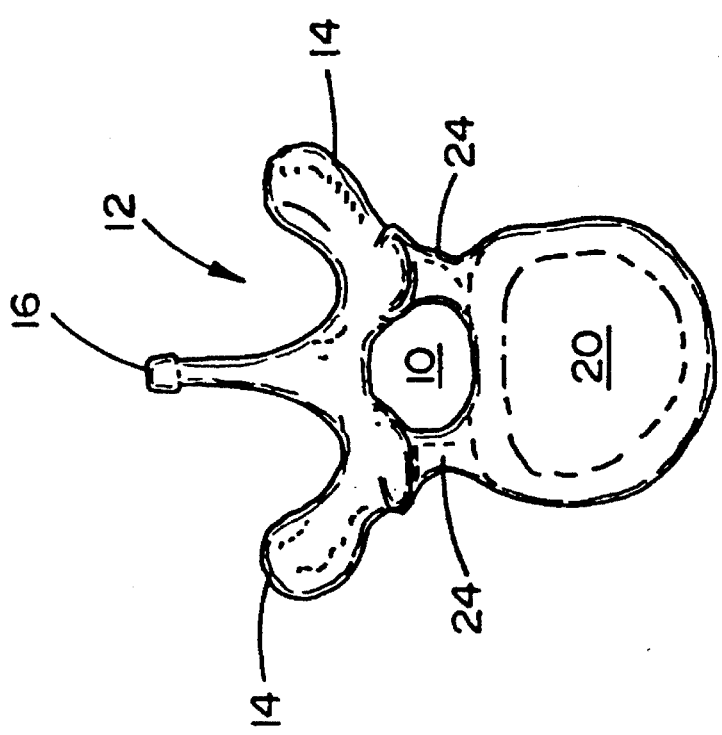
FIG. 1 is a top view of a vertebral bone characteristic of those of the cervical, thoracic, and lumbar spine.
Figure 3:
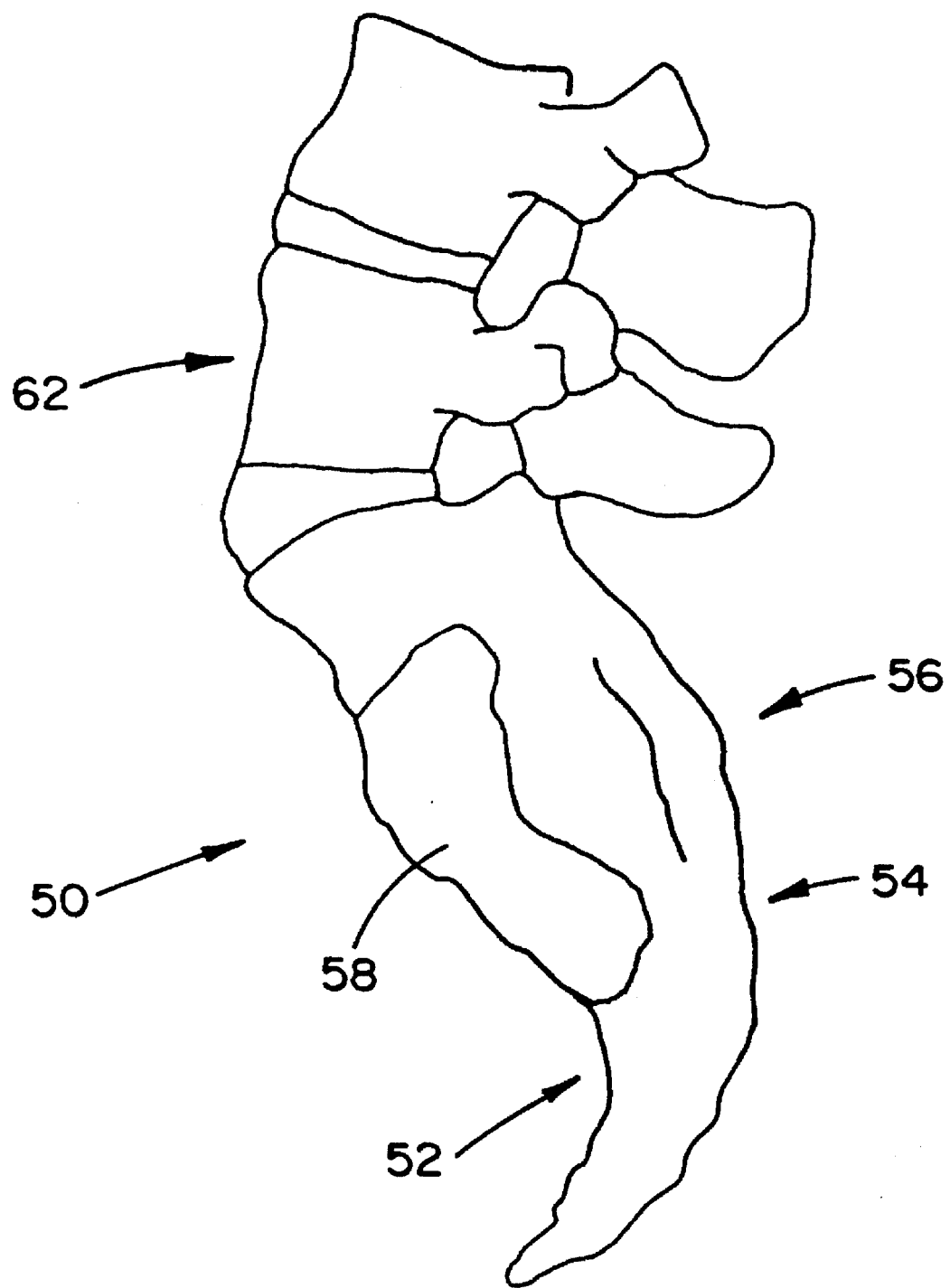
FIG. 3 is a side view of a sacral body.
Figure 4:
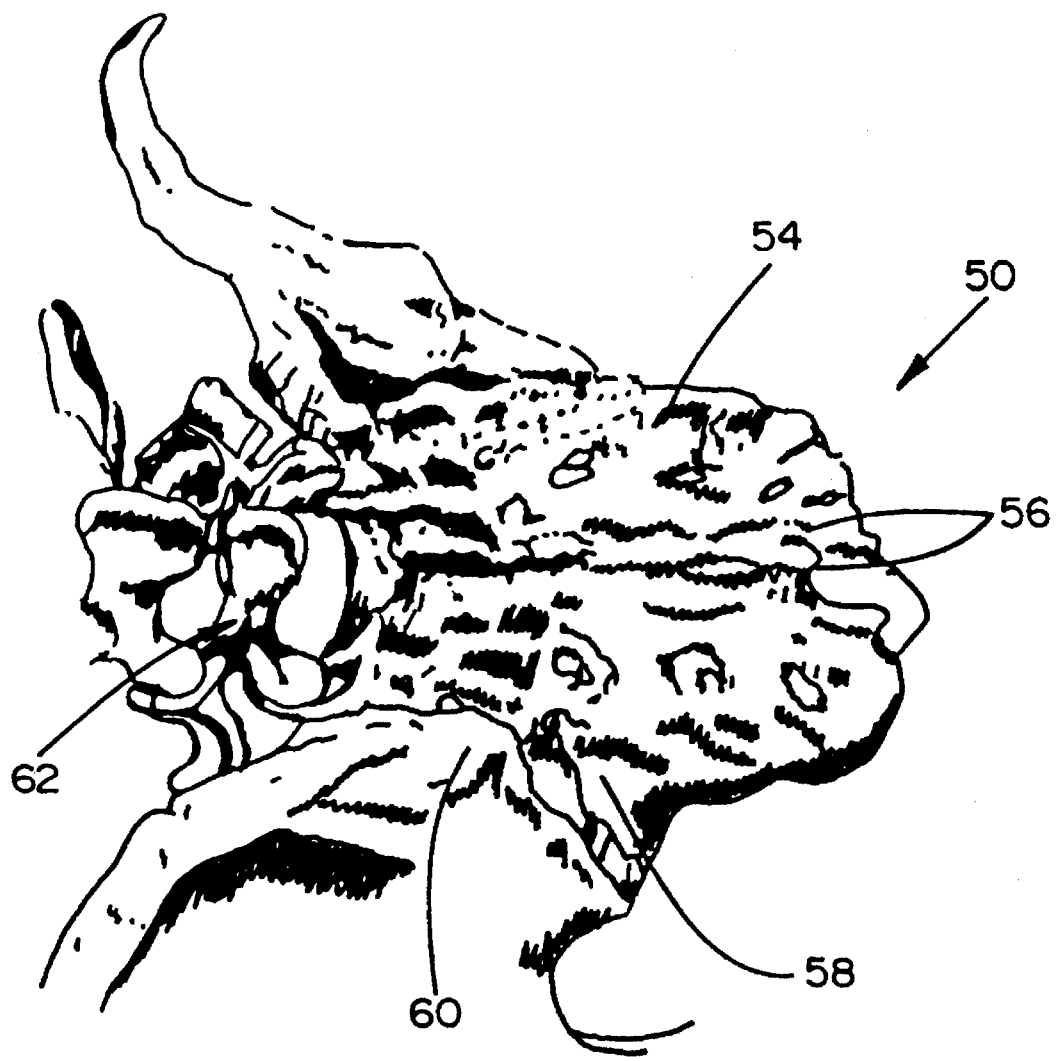
FIG. 4 is a perspective view of a sacral body as it is laterally coupled with the pelvis.
Figure 5:
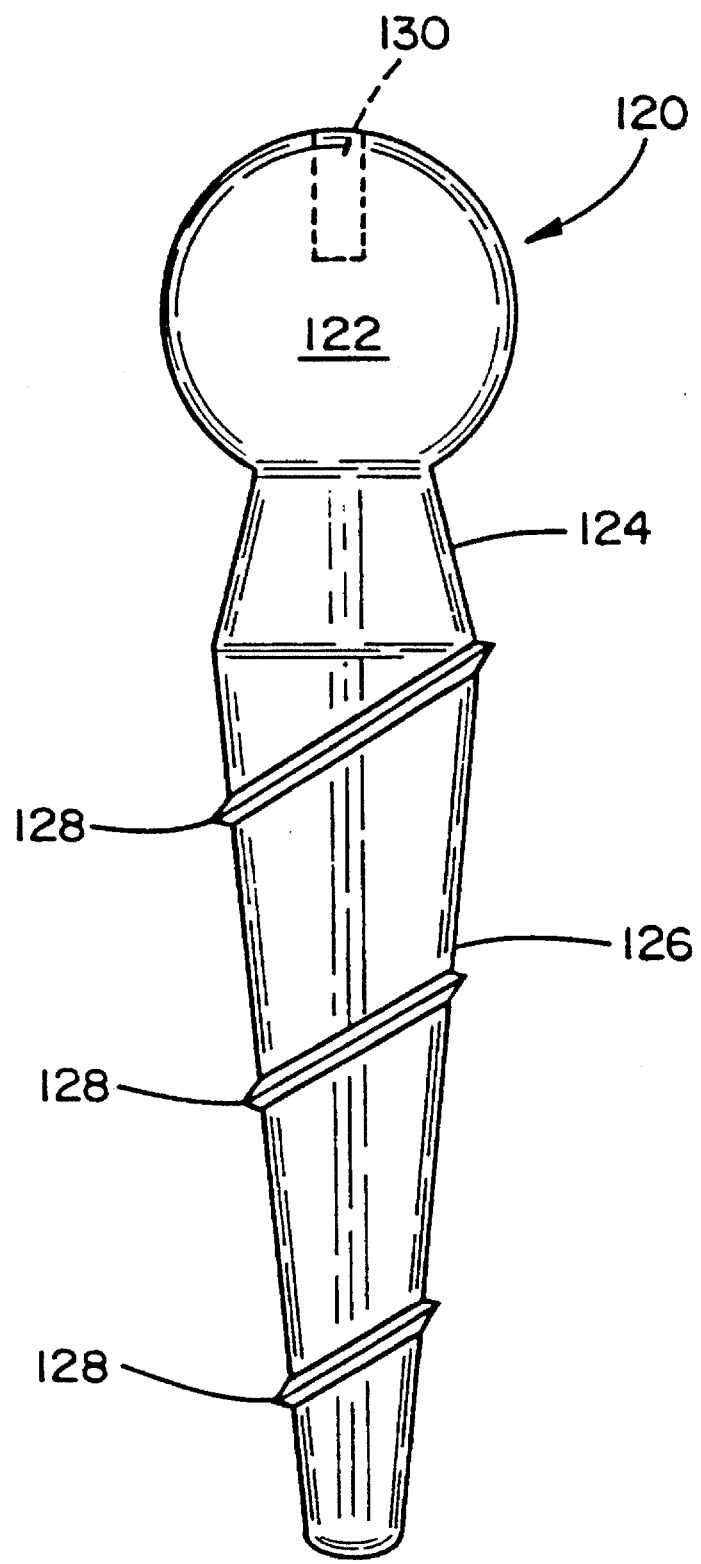
FIG. 5 is a side view of a screw having a polyaxial head which is an aspect of the present invention.

Referring now to FIG. 5, a side view of the screw portion of the present invention, comprising a curvate head, is shown. The screw 120 comprises a head portion 122, a neck 124, and a shaft 126. In FIG. 5, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a semi-spherical shape, which has a recess 130 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 122 (as shown in the two dimensional illustration of FIG. 5) includes at least 270 degrees of a circle.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a flat-headed screwdriver, a crossed recess for a phillips head screwdriver, or most preferably, a hexagonally shaped hole for receiving an allen wrench. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the diameter of the semi-spherical head 122, it is also preferable that the neck 124 of the screw 120 be narrower than the widest portion of the shaft 126. This preferable dimension permits the screw to be locked at a variety of angles while still being securely joined to the coupling element (embodiments of which are shown in FIGS. 6, 7, 10–12, and 14).

Figure 6:
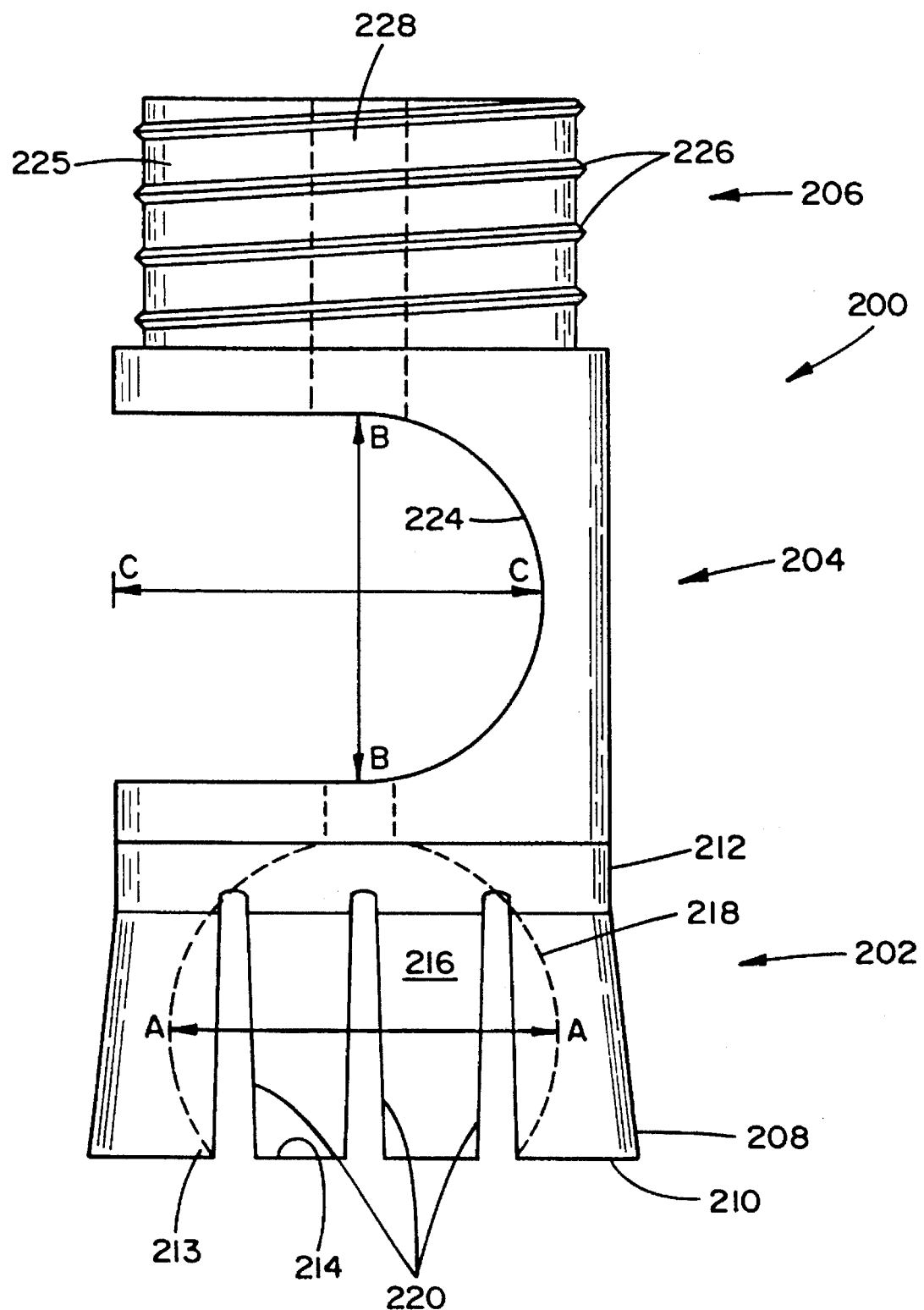
FIG. 6 is a side view of the coupling element of a first embodiment of the present invention.

Referring now to FIG. 6, a first embodiment of the coupling element 200 of the present invention is shown in a side view, wherein critical features of the interior of the element are shown in phantom. The coupling element 200 comprises a generally cylindrical body which may be conceptually separated into a lower portion 202, an intermediate portion 204, and an upper portion 206, each of which shall be described more fully hereinbelow.

First, with respect to the lower portion 202, the exterior surface 208 of the body is tapered in the elongate direction such that the body is wider at the bottom 210 of the lower portion 202 than at the top 212 thereof. The bottom 210 of the element includes an opening 214, defined by annular lip 213, which forms the mouth of an interior chamber 216. The diameter of the opening 214, when otherwise unaffected by external deflecting forces, is more narrow than the maximum diameter A—A of the interior chamber 216. The interior chamber 216 has a generally curvate inner surface 218 which is correspondingly shaped to receive the semi-spherical head 122 of the screw 120.

The exterior surface of the lower portion 202 includes a series of slots 220 which extend vertically upward from the bottom 210 of the element to a point which is closer to the top 212 of the lower portion 202 than the maximum horizontal diameter A—A of the interior chamber. The slots 220 are provided in order that the application of an external deflecting force may widen or narrow the opening 214 therein permitting the insertion of an object, such as the head 122 of the polyaxial screw 120, which is larger than the undeflected diameter of the opening 214, or conversely, providing for the retention of an object such as the same.

The intermediate portion 204 of the generally cylindrical body of the coupling element 200 includes a large removed section which forms a horizontal channel, therein forming a rod receiving locus 222 in the side of the coupling element 200. The rod receiving locus 222 comprises a curvate inner wall 224 which, for example defines a semi-circular cross-section. In the embodiment shown in FIG. 6, the diameter B—B of the semi-circular cross-section of the inner wall 224 is smaller than the horizontal distance C—C which corresponds to the maximum depth of the curvate inner wall 224. The horizontal depth of the inner wall 224 is, therefore, established such that a circular support rod (see FIG. 10) which is positioned in the rod receiving locus 222 may nests fully within the coupling element 200, and does not extend beyond the lateral extent of the element, which would prevent a rod securing sleeve (such as shall be described with reference to FIG. 9) from sliding over the intermediate portion 204 of the element 200 to retain the rod within the rod receiving locus 222.

The upper portion 206 of the coupling element 200 comprises a slightly narrower cylindrical core 225, having a threading 226 thereon. The upper portion 206, and the threading 226 thereon, is ideally suited for receiving a top locking nut (see FIG. 8).

A central bore 228 extends through the upper portion 206, through the intermediate portion 204, and into the lower portion 202. (As shown in the embodiment of FIG. 6, the bore 228 may be interrupted across the open space of the rod receiving locus 222, however, the passage defined thereby is not interrupted.) The bore 228, therefore, provides a linear passage through which a user may insert a screw-driving tool to access the interior chamber 216, and any structural element therein.

Figure 7:
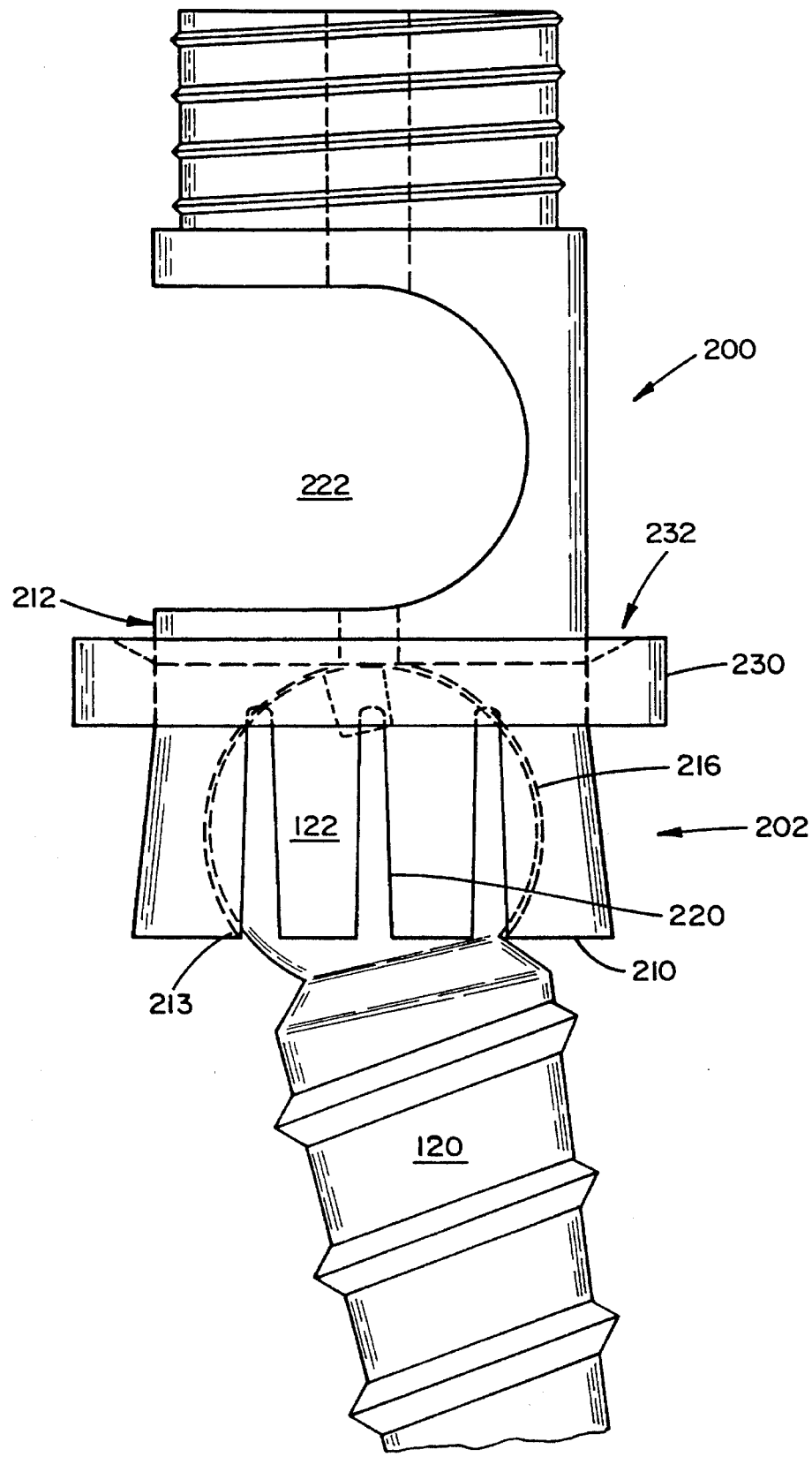
FIG. 7 is a side view of the coupling element shown in FIG. 7, having the screw shown in FIG. 5 inserted into the interior chamber therein, and including a locking ring in its unsecured position.

Referring now to FIG. 7, the coupling element 200, as described more fully with respect to FIG. 6, is shown in a side view, wherein the head 122 of the screw 120 has been received within the interior chamber 216, and a locking ring 230 is shown in its pre-locked position about the top 212 of the lower portion 202. The head 122 of the screw 120 is rotationally free to move relative to the coupling element, however, it is prevented from fully separating from the coupling element and the interior chamber 216 by the annular lip 213 at the bottom 210 of the lower portion 202. The locking ring 230 comprises a contiguous annular element having an inner diameter which is equal to the outer diameter of the lower portion 202 at the top 212 thereof. In order to lock the screw 120 into an angle relative to the coupling element 200, therein eliminating the freedom of the screw 120 to swing relative to the coupling element 200, the locking ring must be forced downward relative to the coupling element 200. A dowel, protuberance, or other suitable means may be provided at or above the top 212 of the lower portion 202 so that the ring 230 may not be easily moved upward, and thereby preventing separation of the locking ring during handling prior to use. The top surface 232 of the locking ring 230 is designed to mate easily with the rod securing sleeve (see FIG. 9).

Figure 8:
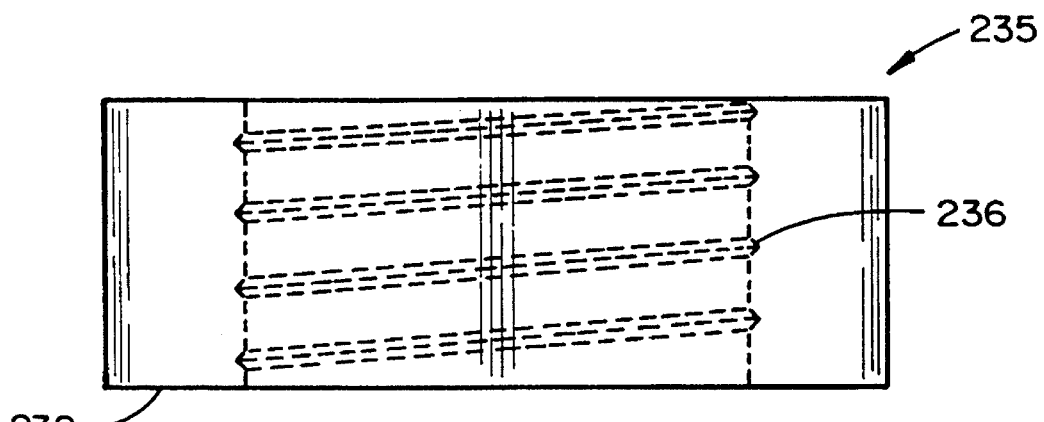
FIG. 8 is a side cross-sectional view of the top locking nut of the present invention.
Figure 9:
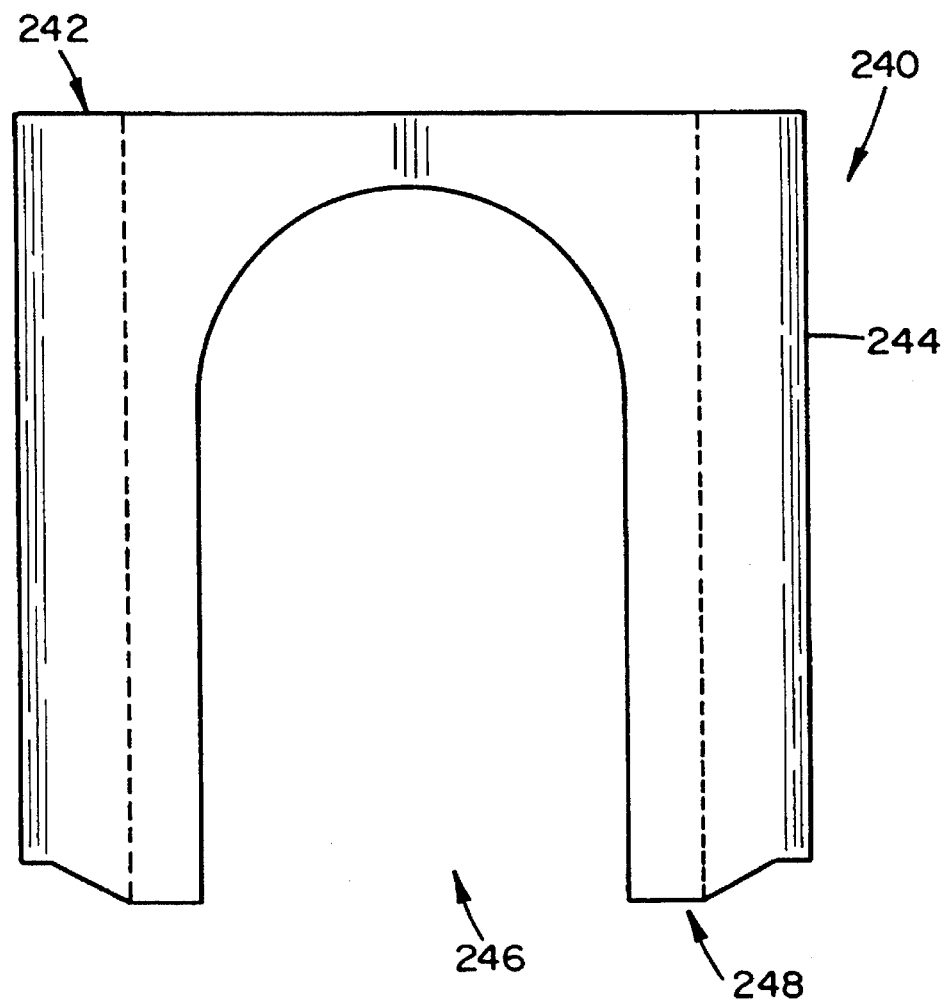
FIG. 9 is a side view of the rod securing sleeve of the first embodiment, shown along a direction wherein the vertically oriented slots thereof are aligned perpendicular to the plane of view.

Referring now to FIGS. 8 and 9, a top locking nut 235 and the rod securing sleeve 240 of the first embodiment are shown in side cross-section views. Referring specifically to FIG. 9, the rod securing sleeve 240 comprises a hollow cylindrical body 244 having diametrically opposing vertical slots 246, which together define a passage through the bottom of the sleeve for the positioning of a rod therethrough. The opposing vertical slots 246 divide the bottom of the sleeve into two downwardly extending members and provide the sleeve 240 with a u-shaped cross-section, as illustrated in FIG. 9. The interior diameter of the sleeve 240 is equal to the outer diameter of the coupling element, so that it may be placed over the coupling element. The vertical slots 246 correspond to the channel or rod receiving locus 222 of the intermediate portion 204 of the coupling element 200, such that the support rod which is inserted therein (see FIG. 10) may pass therethrough. The bottom edge 248 of the rod receiving sleeve 240 is designed to seat securely against the upper surface 232 of the locking ring 230.

Referring now to FIG. 8, the nut 235 comprises an inner threading 236 which is intended to mate with the threading 226 on the upper portion 206 of the coupling element 200. The bottom surface 238 of the nut 235 is intended to seat against the top surface 242 of the rod securing sleeve 240, but is permitted to rotate relative to the sleeve, therein providing a means for driving the sleeve 240 downward (as more fully described hereinbelow with respect to the full assembly of the device, and with respect to FIG. 10).

Figure 10:
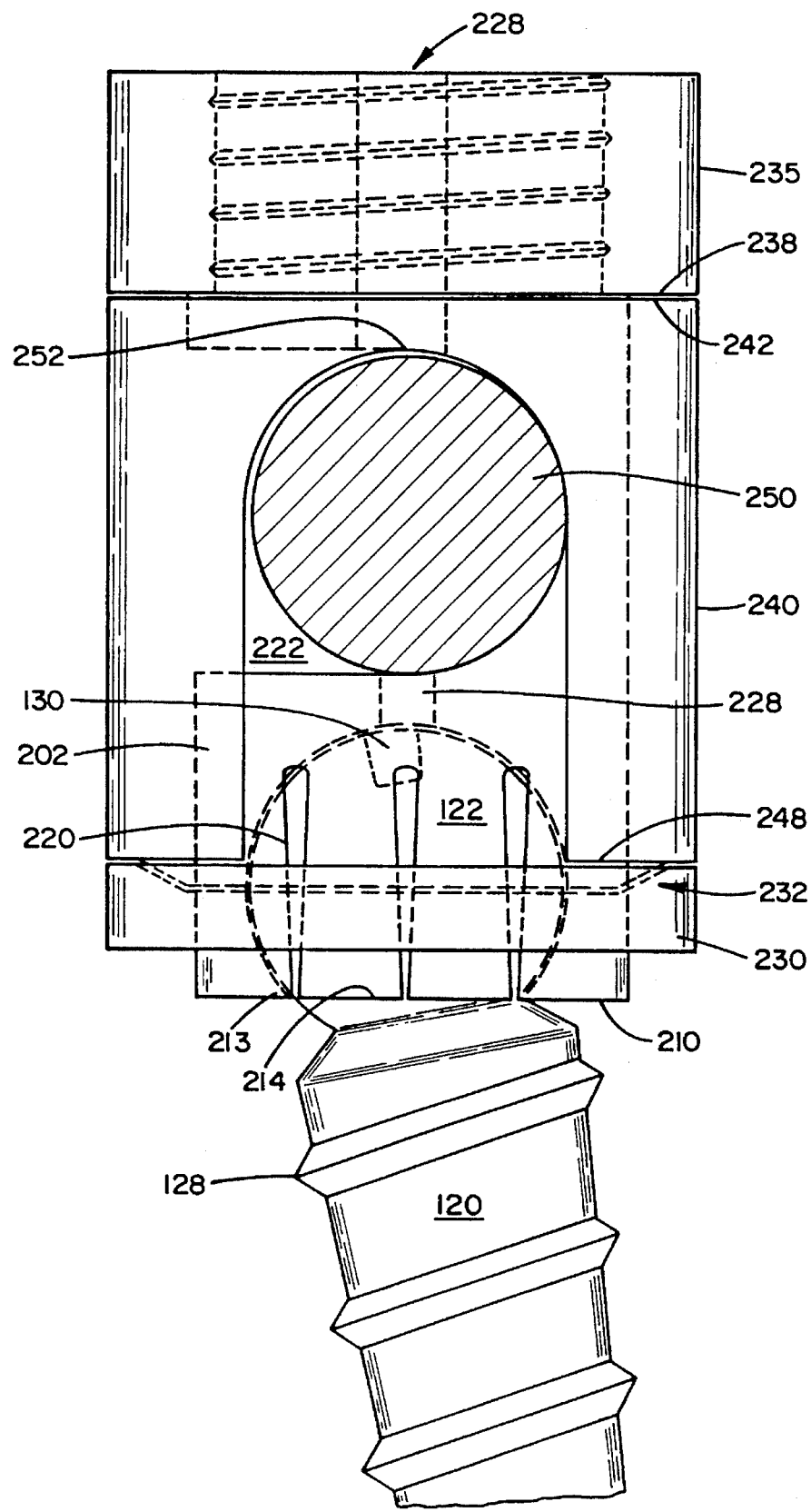
FIG. 10 is a side cross-sectional view of the first embodiment of the present invention in its fully assembled disposition having a rod securely locked therein.

With reference now to FIG. 10, which shows a side view of the fully locked coupling element, rod, and screw system, the preferred method of implantation and assembly is described hereinbelow. First, a pre-drilled hole is provided in the bone, into which it is desired that the screw 120 be disposed. The hole may be pre-tapped, or the external threading 128 of the screw 120 may include a self-tapping lead edge. In either event, the head 122 of the screw 120 is inserted into the interior chamber 216 of the coupling element 200. At this point in the assembly process, the locking ring 230 has not yet been forced downward along the outwardly tapered lower portion 202 (as shown in FIG. 7) thereby providing the screw 120 and the coupling element 200 with the capacity to rotate relative to one another.

By orienting the coupling element 200 and the screw 120 coaxially, the central bore 228 may be aligned with the recess 130 in the head 122 of the screw 120 so that a screw-driving tool may be used to drive the screw into the preformed hole in the bone.

Subsequent to the screw 120 being driven into the hole, the coupling element 200 may be rotated relative to the screw 120, to an angle such that support rod 250 may be properly nested within the rod receiving locus 222. After the rod 250 is appropriately positioned, the rod securing sleeve 240 is dropped over the element, such that the rod extends outward through the diametrically opposed vertical slots 246 in the sleeve 240. At this stage of the assembly, the head 122 and the coupling element 200 remain rotationally free, and the locking ring 230 remains positioned at the top 212 of the lower portion 202 of the element. The rod securing sleeve 240 is prevented from fully descending onto the coupling element 200 as the bottom edge 248 thereof mates to, and is prevented from moving by, the top surface 232 of the locking ring 230.

Once the proper angulation of the coupling element to the screw 120, and the secure nesting of the rod 250 within the receiving locus 222, have been established, the top locking nut 235 is threaded onto the upper portion 206 of the coupling element 200. The lower surface 238 of the nut 235 seats against the top surface 242 of the rod securing sleeve 240. As the nut 235 rotates, and descends relative to the coupling element, the rod securing sleeve 240 is driven downward. This motion forces the locking ring 230 downward as well, relative to the lower portion 202 of the coupling element 200. By descending along the tapered lower portion 202 of the element, the locking ring 230 provides an inwardly directed deflecting force which causes the slots 220 in the lower portion 202 of the element to narrow so that the ring may proceed downward. This deflection inward causes the inner surface 218 of the interior chamber 216 to crush lock against the head 122 of the screw 120. This clamping force locks the angulation of the screw 120 to the coupling element 200. In addition, the downward force of the nut 235 against the rod securing sleeve 240 further causes the uppermost curve 252 of the vertical slot 246 of the sleeve 240 to lock the rod 250. This locking prevents the rod 250 from sliding relative to the assembled structure (along an axis which is perpendicular to the plane of FIG. 10). The full insertion of the top locking nut 235, therefore, locks the rod 250 to the coupling element 200, as well as the screw 120 to the coupling element 200.

Figure 11:
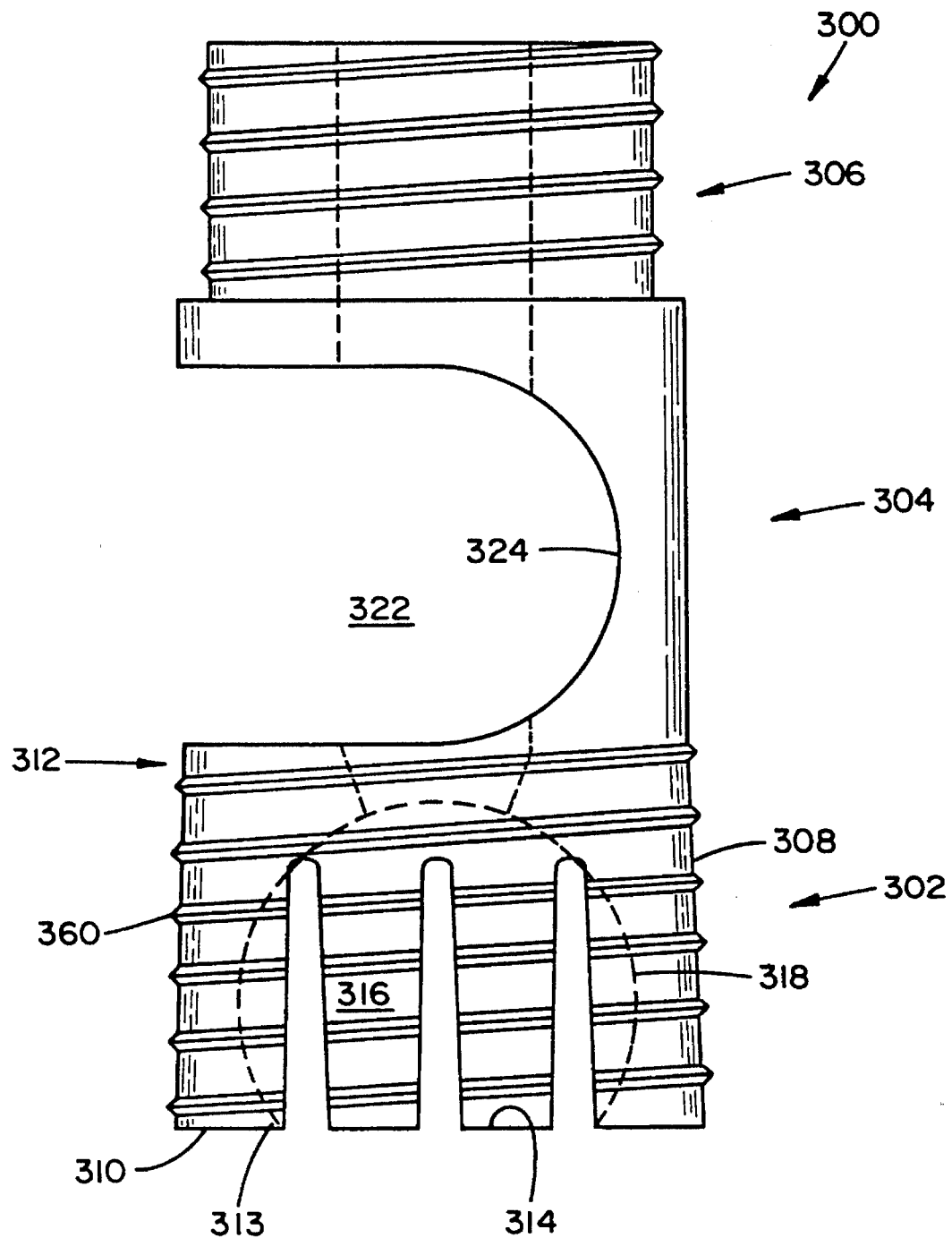
FIG. 11 is a side view of the coupling element of a second embodiment of the present invention.

Referring now to FIG. 11, which shows an alternative coupling element 300, a second embodiment of the present invention is provided, wherein the lower portion 302 of the coupling element 300 includes a threading 360. In this embodiment the locking ring (see FIG. 12) may be independently translated downward to lock the angulation of the screw to the coupling element, without regard to a rod securing sleeve which may be placed over the rod and coupling element subsequently. More specifically, with respect to the coupling element 300 itself, and to the lower portion 302, the exterior surface 308 of the body is tapered in the elongate direction such that the body is wider at the bottom 310 than at the top 312 thereof. The bottom 310 of the element includes an opening 314, defined by annular lip 313, which forms the mouth of an interior chamber 316. As is the case with the first embodiment, the diameter of the opening 314, when otherwise unaffected by external deflecting forces, is more narrow than the maximum diameter of the interior chamber 316. The interior chamber 316 has a generally curvate inner surface 318 which is correspondingly shaped to receive the semi-spherical head 122 of the screw 120.

The exterior surface 308 of the lower portion 302 includes a threading 360 and a series of slots 320 which extend vertically upward from the bottom 310 of the element to a position above the widest point of the interior chamber 316. The slots 320 are provided in order that the application of an external deflecting force may widen or narrow the opening 314 therein permitting the insertion of an object which is larger than the undeflected diameter of the opening 314, or conversely, providing for the retention of an object which is smaller than the undeflected diameter of the opening 314.

The intermediate portion and upper portions 304,306 of the generally cylindrical body of the coupling element 300 are equivalent to those portions 304,306, respectively, of the first embodiment. The intermediate portion 304 includes a large horizontal channel, which comprises a rod receiving locus 322 in the side of the coupling element 300, having a curvate inner wall 224. The depth of the inner wall 324 is established such that a circular support rod (see FIG. 14) may be fully nested within the rod receiving locus 322 and does not extend beyond the lateral extent of the element. This ensures the proper insertion of the rod securing sleeve (such as shall be described with reference to FIG. 13), so that it may slide over the intermediate portion 304 of the element 300 to retain the rod within the rod receiving locus 322.

The upper portion 306 of the coupling element 300 comprises a slightly narrower cylindrical core 325, having a threading 326 thereon. The upper portion 306, and the threading 326 thereon, is ideally suited for receiving a top locking nut (see FIG. 8). In addition, as is the case with the first embodiment, a central bore 328 extends through the upper portion 306, through the intermediate portion 304, and into the lower portion 302. The bore 328 provides a linear passage through which a user may insert a screw-driving tool to access the interior chamber 316, and the screw head 120 therein.

Figure 12:
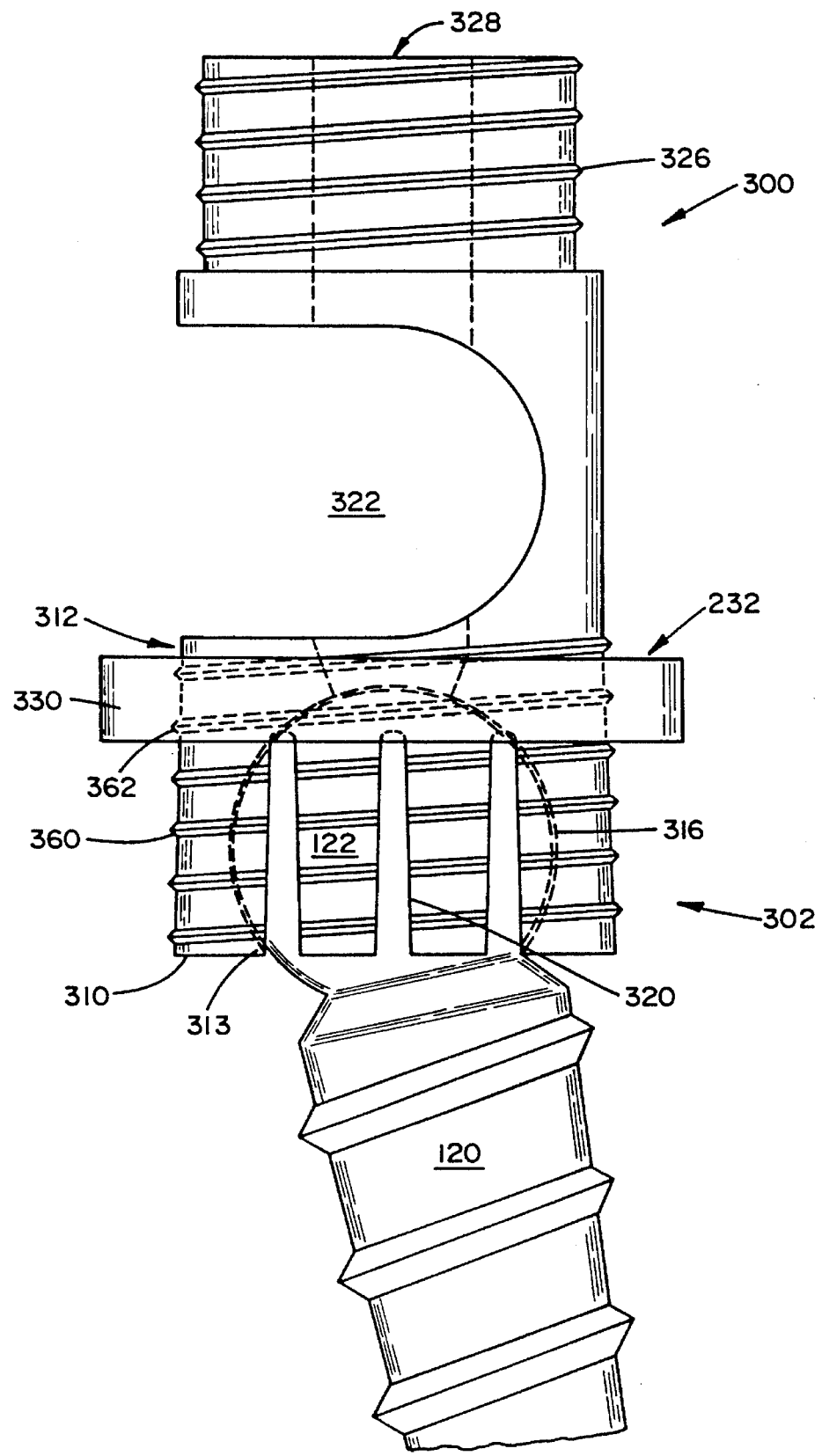
FIG. 12 is a side view of the coupling element shown in FIG. 11, having the screw shown in FIG. 5 inserted into the interior chamber therein, and including a threaded locking ring in its unsecured position.

Referring now to FIG. 12, the coupling element 300, as described more fully with respect to FIG. 11, is shown in a side view, wherein the head 122 of the screw 120 has been received within the interior chamber 316, and a threaded locking ring 330 is shown in its pre-locked position about the top 312 of the lower portion 302. The head 122 of the screw 120 is rotationally free to move relative to the coupling element, within the interior chamber 316, however, it is prevented from fully separating from the coupling element by the annular lip 313 at the bottom 310 of the lower portion 302. The locking ring 330 comprises a contiguous annular element having an inner diameter which is equal to the outer diameter of the lower portion 302 at the top 312 thereof, and a threading 362 on the inner surface thereof. In order to lock the screw 120 into an angle relative to the coupling element 300, therein eliminating the freedom of the screw 120 to swing relative to the coupling element 300, the locking ring 330 may be rotated so that it translates downward along the threading 360 of the lower portion 302. The threading 360 of the lower portion 302 may include an upper slide prevention means, for example a thickened thread (not shown) so that the ring 330 may not be easily moved upward, and thereby preventing separation of the locking ring during handling prior to use. In the alternative, a dowel or protuberance may be provided to serve the equivalent function. The top surface 332 of the locking ring 330 is designed to mate easily with the rod securing sleeve (see FIG. 14).

Figure 13:
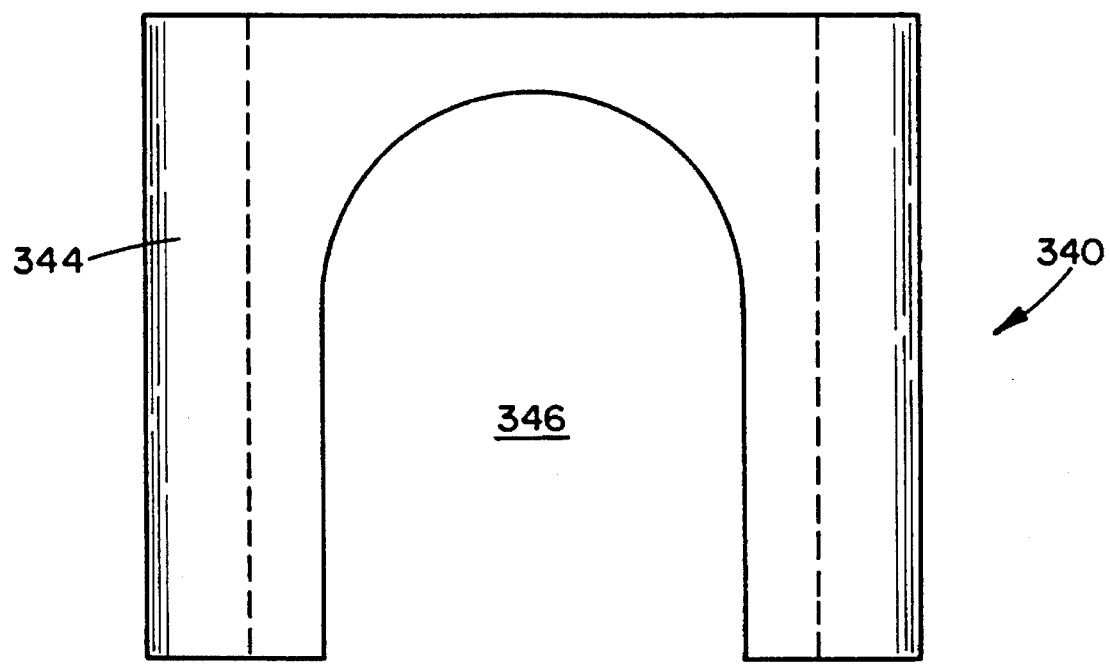
FIG. 13 is a side view of the rod securing sleeve of the second embodiment, shown along a direction wherein the vertically oriented slots thereof are aligned perpendicular to the plane of view.

Referring now to FIG. 13, a rod securing sleeve 340 of the second embodiment is shown in side cross-section views. Similar to the sleeve 240 of the first embodiment, rod securing sleeve 340 comprises a hollow cylindrical body 344 having diametrically opposing vertical slots 346, which together define a passage through the sleeve 300 for the positioning of a rod therethrough. The interior diameter of the sleeve 340 is equal to the outer diameter of the coupling element, so that it may be placed thereover. The vertical slots 346 correspond to the channel or rod receiving locus 322 of the intermediate portion 304 of the coupling element 300, such that the support rod which is inserted therein (see FIG. 14) may pass therethrough. The bottom edge 348 of the rod receiving sleeve 340 of the second embodiment may be designed to fit securely with the upper surface 332 of the locking ring 330, or it may simple seat against it for the purposes of preventing it from backing up the threads 360 of the coupling element 300.

Figure 14:
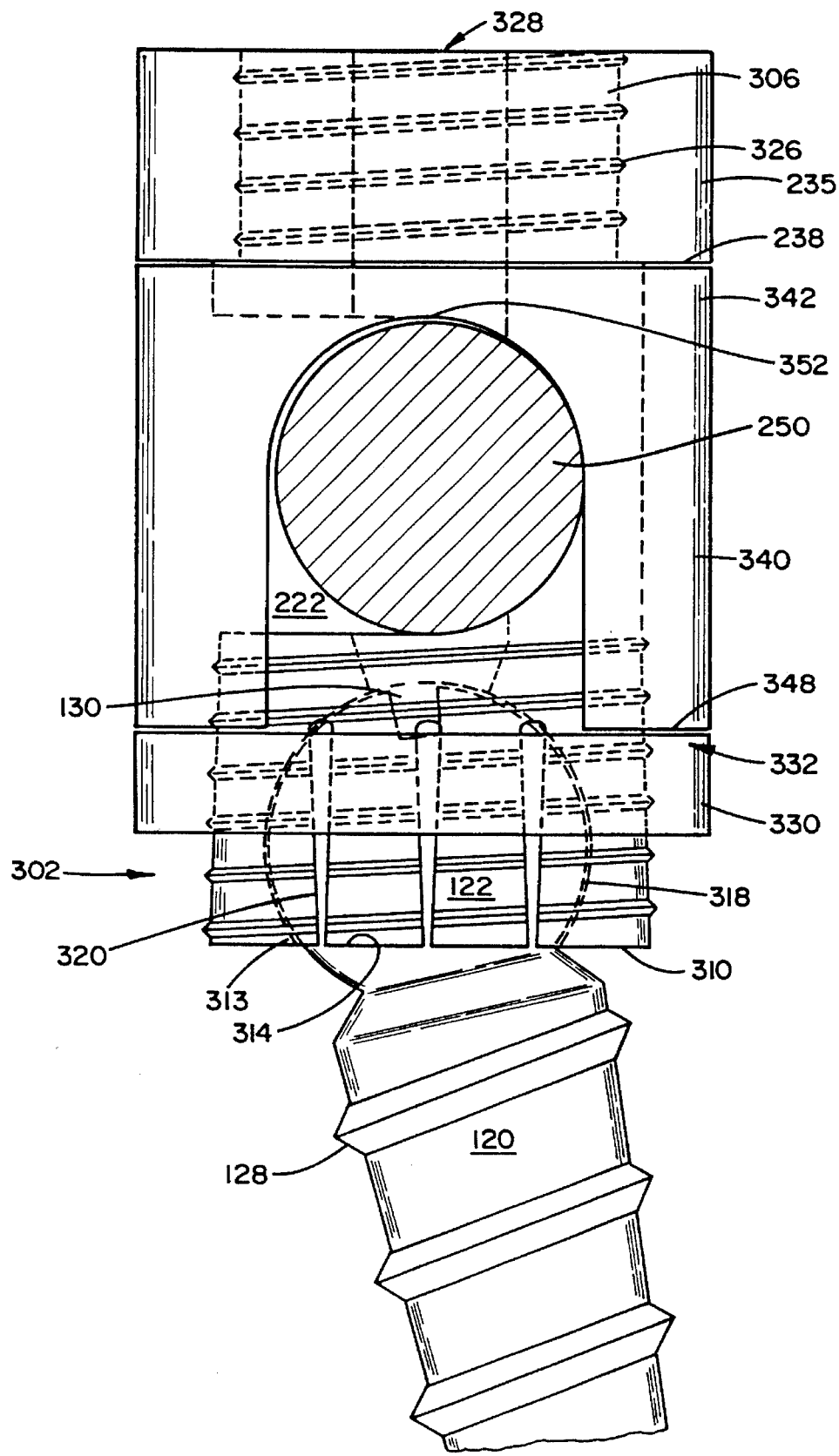
FIG. 14 is a side cross-sectional view of the second embodiment of the present invention in its fully assembled disposition with a rod securely coupled thereto.

With reference now to FIG. 14, which shows a side view of the fully locked coupling element 300, rod 250, and screw 120 assembly, the preferred method of implantation and assembly is described hereinbelow. As described with respect to the implantation of the first embodiment, prior to its insertion into the bone, the head 122 of the screw 120 is positioned in the interior chamber 316 of the coupling element 300. A hole is then drilled into the bone, into which the screw 120 is to be inserted. The coupling element 300 and the screw 120 are rotated relative to one another so that the screw-driving tool may access the recess 130 in the head 122 for easy implantation. Once the screw 120 has been fully inserted, however, the coupling element 300 is moved relative to the coupling element 300 into the ideal orientation for receiving the rod 250. At this point, the threaded locking ring 330 is rotated downward to lock the screw 120 to the coupling element by forcing the vertical slots 346 in the lower portion 302 together, therein crush locking the interior surface 318 to the external surface of the head 122.

Subsequent to the locking of the screw 120 to the coupling element 300 the support rod 250 is positioned within the rod receiving locus 322. Once the rod 250 is properly nested, the rod securing sleeve 340 is dropped over the assembly such that the rod extends outward through the diametrically opposed vertical slots 346 in the sleeve 340. Unlike in the case of the first embodiment, the rod securing sleeve 340 may fully descend onto the coupling element 300 without being prevented from doing so by virtue of the locking ring's 330 presence.

In order to fully lock the rod 250 to the coupling element 300, and to lock the rod securing sleeve 340 in position, the top locking nut 235 is threaded onto the upper portion 306 of the coupling element 300. The lower surface 238 of the nut 235 seats against the top surface 342 of the rod securing sleeve 340 preventing it from translating upward. In addition, the nut 235 causes the uppermost curve 352 of the vertical slot 346 of the sleeve 340 to crush lock to the rod 250. This locking prevents the rod 250 from sliding relative to the assembled structure (along an axis which is perpendicular to the plane of FIG. 14). The downward force of the descending top locking nut 235, therefore, locks the rod 250 to the coupling element 300, and the threaded locking ring locks the screw 120 to the coupling element 300. It is preferable that the bottom surface 348 of the rod securing sleeve 340 seat against the upper surface 332 of the locking ring 330, to prevent the ring 330 from translating back up the lower portion. It is understood, however, that unlike the first embodiment, the locking of the screw 120 to the coupling element 300 by the locking ring 330 may be entirely separate and independent from the locking of the sleeve 340 and rod 250 to the coupling element 300 by the top locking nut 235. It is understood that the threading 360, along which the locking ring 330 is rotated, and the threading 326 along which the top locking nut 235 is rotated may be oppositely oriented so as to prevent sympathetic loosening in vivo.

While there has been described and illustrated several embodiments of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A polyaxial screw and coupling element assembly for use with orthopedic rod implantation apparatus, comprising:

a screw having a curvate head;

a coupling element including an expandable and contractable interior chamber for receiving therein said curvate head, said interior chamber further having an expandable and contractable opening for receiving therethrough said currate head, a rod receiving locus for receiving therein a rod of said orthopedic rod implantation apparatus into the side thereof, and a surface threading disposed on an upper exterior portion thereof;

a locking ring mounted around said coupling element, the downward translation of said ring providing a force which causes said interior chamber and said opening thereof to contract, therein locking the screw to the coupling element;

a rod securing sleeve, positionable around, and in rod securing relationship with, said rod receiving locus for securing said rod therein;

a top locking nut, mateable with said surface threading.

2. The coupling assembly as set forth in claim 1, wherein said curvate head is semi-spherical.

3. The coupling assembly as set forth in claim 1, wherein said coupling element further comprises at least one vertical slot extending upward from said opening, therein rendering said interior chamber and said opening expandable and contractable.

4. The coupling assembly as set forth in claim 3, wherein a portion of said coupling element which contains said interior chamber comprises an exterior surface taper, said portion being wider at said opening, whereby the downward translation of said locking ring causes the interior chamber and said opening to contract.

5. The coupling assembly as set forth in claim 4, wherein a bottom surface of said top locking nut seats against a top surface of said rod securing sleeve, the downward translation of said top locking nut causes said rod securing sleeve to crush lock said rod to said coupling element.

6. The coupling assembly as set forth in claim 5, wherein a bottom surface of said rod securing sleeve seats against a top surface of said locking ring, whereby the downward translation of said nut on said exterior threading of said coupling element causes the downward translation of said locking ring to crush lock the screw within said interior chamber.

7. The coupling element as set forth in claim 4, wherein said coupling element comprises a second threading disposed about an outer surface thereof, at least a portion of which includes the at least one vertical slot, and wherein said locking ring includes a threading on an interior surface thereof, mateable with said second threading, whereby said locking ring may be downwardly translated on said second threading.

8. A polyaxial screw and coupling element assembly for use with orthopedic rod implantation apparatus, comprising:

a screw having a curvate head;

a coupling element having lower, intermediate, and upper portions thereof, said lower portion including a taper wherein the bottom of the portion is wider than the top, said coupling element including at least one vertical slot formed in said lower portion extending upward from a bottom of said lower portion, an opening in said bottom of said lower portion, for receiving therethrough said curvate head, said opening being expandable and contractable via forces applied to said at least one vertical slot;

an interior chamber disposed within said lower portion, for receiving therein said curvate head, a rod receiving locus formed in the side of said intermediate portion for receiving therein a rod of said orthopedic rod implantation apparatus, and an exterior threading disposed on said upper portion;

a locking ring mounted about said lower portion, the downward translation of said ring applying an inward force to said at least one vertical slot and therein locking the screw to the coupling element;

a rod securing sleeve comprising a hollow cylindrical body, having a opposing vertical slots, said sleeve being positionable about said intermediate portion for securing said rod within said intermediate portion, wherein said rod passes through said vertical slots of said sleeve; and a top locking nut which is mateable with said exterior threading.

9. The coupling assembly as set forth in claim 8, wherein a bottom surface of said top locking nut seats against a top surface of said rod securing sleeve, the downward translation of said top locking nut causes said rod securing sleeve to crush lock said rod to said coupling element.

10. The coupling assembly as set forth in claim 9, wherein a bottom surface of said rod securing sleeve seats against a top surface of said locking ring, whereby the downward translation of said nut on said exterior threading of said coupling element causes the downward translation of said locking ring to crush lock the screw within said interior chamber.

11. The coupling element as set forth in claim 8, wherein said coupling element comprises a second threading disposed about an outer surface thereof, at least a portion of which includes the at least one vertical slot, and wherein said locking ring includes a threading on an interior surface thereof, mateable with said second threading, whereby said locking ring may be downwardly translated on said second threading.

12. An orthopedic rod implantation apparatus, comprising:
   at least one elongate rod;
   a plurality of polyaxial coupling assemblies, each of said assemblies including
      a screw having a curvate head;
      a coupling element having, an expandable and contractable interior chamber for receiving therein said curvate head, said interior chamber having an expandable and contractable opening for receiving therethrough said curvate head, a rod receiving locus for receiving therein a rod of said orthopedic rod implantation apparatus into the side thereof, and a surface threading disposed on an upper exterior portion thereof;
      a locking ring mounted around said coupling element, the downward translation of said ring providing a force which causes said interior chamber and said opening thereof to contract, therein locking the screw to the coupling element;
      a rod securing sleeve, positionable around, and in rod securing relationship with, said rod receiving locus for securing said rod therein;
      a top locking nut, mateable with said surface threading.

13. The apparatus as set forth in claim 12, wherein said curvate head is semi-spherical.

14. The apparatus as set forth in claim 12, wherein said coupling element further comprises at least one vertical slot extending upward from said opening, therein rendering said interior chamber and said opening expandable and contractable.

15. The apparatus as set forth in claim 14, wherein a portion of said coupling element which contains said interior chamber comprises an exterior surface taper, said portion being wider at said opening, whereby the downward translation of said locking ring causes the interior chamber and said opening to contract.

16. The apparatus as set forth in claim 15, wherein a bottom surface of said top locking nut seats against a top surface of said rod securing sleeve, the downward translation of said top locking nut causes said rod securing sleeve to crush lock said rod to said coupling element.

17. The apparatus as set forth in claim 16, wherein a bottom surface of said rod securing sleeve seats against a top surface of said locking ring, whereby the downward translation of said nut on said exterior threading of said coupling element causes the downward translation of said locking ring to crush lock the screw within said interior chamber.

18. The apparatus as set forth in claim 15, wherein said coupling element comprises a second threading disposed about an outer surface thereof, at least a portion of which includes the at least one vertical slot, and wherein said locking ring includes a threading on an interior surface thereof, mateable with said second threading, whereby said locking ring may be downwardly translated on said second threading.

* * * * *